US012135304B2

(12) United States Patent
Johnston et al.

(10) Patent No.: US 12,135,304 B2
(45) Date of Patent: Nov. 5, 2024

(54) ELECTROANALYTICAL INSTRUMENT FOR DETERMINING BY AMPEROMETRY THE PRESENCE OR QUANTITY OF AN ANALYTE IN AN AQUEOUS SAMPLE

(71) Applicant: Palintest Limited, Kingsway (GB)

(72) Inventors: Simon Richard Johnston, Chollerton (GB); Kevin McDermott, Heaton (GB)

(73) Assignee: PALINTEST LIMITED, Kingsway (GB)

( * ) Notice: Subject to any disclaimer, the term of this patent is extended or adjusted under 35 U.S.C. 154(b) by 763 days.

(21) Appl. No.: 16/641,744

(22) PCT Filed: Oct. 15, 2018

(86) PCT No.: PCT/GB2018/052956
§ 371 (c)(1),
(2) Date: Feb. 25, 2020

(87) PCT Pub. No.: WO2019/077321
PCT Pub. Date: Apr. 25, 2019

(65) Prior Publication Data
US 2020/0249192 A1    Aug. 6, 2020

(30) Foreign Application Priority Data

Oct. 20, 2017  (GB) .................................... 1717286

(51) Int. Cl.
*G01N 27/28* (2006.01)
*G01N 27/416* (2006.01)
(Continued)

(52) U.S. Cl.
CPC ....... *G01N 27/286* (2013.01); *G01N 27/4161* (2013.01); *G01N 27/49* (2013.01); *G01N 33/182* (2013.01)

(58) Field of Classification Search
CPC .. G01N 27/286; G01N 27/4161; G01N 27/49; G01N 33/182
See application file for complete search history.

(56) References Cited

U.S. PATENT DOCUMENTS

| 6,290,827 B1 * | 9/2001 | Johansson ............. G01N 27/49 |
| | | 324/447 |
| 2006/0200045 A1 * | 9/2006 | Roe ................... A61B 5/150297 |
| | | 600/583 |

(Continued)

FOREIGN PATENT DOCUMENTS

| CN | 205449867 U |   | 8/2016 |
| CN | 205620346 U | * | 10/2016 |

(Continued)

OTHER PUBLICATIONS

Anonymous, ChlordioXense User Manual, Nov. 8, 2016, XP055527682 (Year: 2016).*

(Continued)

*Primary Examiner* — James Lin
*Assistant Examiner* — Vivian A Tran
(74) *Attorney, Agent, or Firm* — Harness, Dickey & Pierce, PLC

(57) ABSTRACT

The present invention relates to an electroanalytical instrument for determining by amperometry (eg chronoamperometry) the presence or quantity (eg concentration) of an analyte in an aqueous sample, comprising a sealed housing, an elongate pivotal arm mounted on the sealed housing, wherein the elongate pivotal arm houses a potentiostat, and a pivotal forearm joined pivotally to the elongate pivotal arm, which is connectable to an electrochemical sensor. By flexing the pivotal forearm, the electrochemical sensor may be electrically connected to the potentiostat. By flexing the (Continued)

elongate pivotal arm, the electrochemical sensor is immersed in the aqueous sample in the sealed housing.

11 Claims, 8 Drawing Sheets

(51) Int. Cl.
   *G01N 27/49* (2006.01)
   *G01N 33/18* (2006.01)

(56) References Cited

U.S. PATENT DOCUMENTS

2008/0283396 A1   11/2008   Wang et al.
2018/0325432 A1*  11/2018   Harttig .................. H02J 7/0044

FOREIGN PATENT DOCUMENTS

GB         2549281 A       10/2017
WO     WO-2007026152 A1 *  3/2007   ........... G01N 27/307

OTHER PUBLICATIONS

International Search Report and Written Opinion issued in PCT/GB/2018/052956, mailed Dec. 14, 2018; ISA/EP.
Anonymous: "ChlordioXense User Manual", Nov. 8, 2016 (Nov. 8, 2016), XP055527682, Retrieved from the Internet: URL:https://web.archive.org/web/20161108083131if_/http://www.palintest.com:80/application/files/1914/5548/0608/INST.37_-_ChlordioXense-English A6.pdf [retrieved on Nov. 27, 2018] the whole document.
UK Search Report under Section 17 for Application No. GB 1717286.7, dated Apr. 17, 2018.

* cited by examiner (d)

(e)

ELECTROANALYTICAL INSTRUMENT FOR DETERMINING BY AMPEROMETRY THE PRESENCE OR QUANTITY OF AN ANALYTE IN AN AQUEOUS SAMPLE

CROSS-REFERENCE TO RELATED APPLICATIONS

This application is a 371 U.S. National Phase of International Application No. PCT/GB2018/052956, filed Oct. 15, 2018, which claims priority to British Patent Application No. 1717286.7, filed Oct. 20, 2017. The entire disclosures of the above applications are incorporated herein by reference.

FIELD

The present invention relates to an electroanalytical instrument for determining by amperometry (e.g., chronoamperometry) the presence or quantity (e.g., concentration) of an analyte (e.g., an oxidant of interest) in an aqueous sample.

BACKGROUND

There is significant ongoing development of low cost, disposable electrochemical sensors for use in the electroanalysis of an environmental sample outside a laboratory. For this purpose, the electrochemical sensor is typically interfaced with a portable field instrument in a system which enables the electrochemical sensor to be operated amperometrically. The analysis provides rapid results and facilitates instant decision-making but may be undertaken in challenging environmental conditions which cause inter alia moisture ingress and contamination of sample areas and of electrical contact pins. Moreover, contamination or moisture ingress can result from agitation of the sample through careless handling, condensation due to poor maintenance or as a consequence of the operator having wet or dirty hands. The presence of moisture on the electrical contact pins can cause a short circuit and lead to a significant delay in the use of the electrochemical sensor or even the return of the electrochemical sensor to the manufacturer for servicing or replacement.

SUMMARY

Electrochemical sensors of the type disclosed in WO-A-2007/026152 have been developed with an overall area of working electrode which is small. Typically, the working electrodes are in a dimensional range (50-400 micron) which is sufficient for them to be considered to be microelectrodes. In these electrochemical sensors, a reagent formulation is dried on the microelectrode surface to provide the chemical components essential for specific ion electroanalysis. Once the electrochemical sensor is immersed in a test solution, dissolution takes place to give rise to natural convection of the reagent formulation from the surface into the bulk solution.

Microelectrodes have a number of advantages over macroelectrodes including faster mass transport rates, lower ohmic drop and improved diffusion provided that the gap between adjacent microelectrodes is sufficient to ensure diffusional independence. For electrochemical sensors of this type however, moisture in ingress and contamination can be particularly troublesome because the microelectrodes are typically incorporated onto a relatively small substrate and the distance between the electrical contacts and from the microelectrodes to the electrical contacts is therefore small.

The precise composition of an environmental sample is often unknown. There may be chemical or microbiological toxins associated with the environmental sample of which the operator is unaware. The direct handling of the electrochemical sensor for disposal is therefore potentially hazardous to the operator.

The present invention seeks to improve the performance of an electroanalytical instrument (e.g., a portable field instrument).

Thus viewed from a first aspect the present invention provides an electroanalytical instrument for determining by amperometry (e.g., chronoamperometry) the presence or quantity (e.g., concentration) of an analyte (e.g., an oxidant of interest) in an aqueous sample comprising:

a sealed housing which is compartmentalized, wherein the sealed housing has an exterior compartment defining a receptacle for the aqueous sample and interior compartments;

an elongated pivotal arm mounted pivotally at a proximal end on the sealed housing, wherein the elongated pivotal arm houses a potentiostat;

a pivotal forearm joined pivotally to or near to a distal end of the elongated pivotal arm, wherein in use an electrochemical sensor is mounted in or on an anterior wall of the pivotal forearm and extends inferiorly to the elongated pivotal arm, wherein on an inferior part of the electrochemical sensor there are a reference electrode, a counter electrode and at least one working electrode which is dosed with a reagent formulation for electroanalysis and on a superior part of the electrochemical sensor each of the reference electrode, counter electrode and at least one working electrode terminates in an electrical contact; and a mounting for electrical contact pins which is mounted sealingly on the distal end of the elongated pivotal arm, wherein in use the electrical contact pins are electrically connected to the potentiostat and apply a potential to the electrochemical sensor, wherein the elongated pivotal arm pivots between a fully extended position and a fully flexed position whereat the inferior part of the electrochemical sensor is immersed in the aqueous sample in the receptacle thereby initiating dissolution of the reagent formulation into the aqueous sample and wherein the pivotal forearm pivots between a fully open position whereat the electrical contact pins are exposed and a fully closed position whereat the electrical contacts on the superior part of the electrochemical sensor are in operative contact with the electrical contact pins whereby when the elongated pivotal arm is in the fully flexed position and the pivotal forearm is in the fully closed position the electrochemical sensor interfaces the electrical contact pins and the aqueous sample.

By virtue of a discrete mounting for electrical contact pins being mounted outside the sealed housing, the access to and cleaning of the electrical contact pins does not compromise the water-sensitive electroanalytical components such as the potentiostat housed in the sealed housing. This enables an operator to inspect, dean and dry the electrical contact pins straightforwardly in order for the instrument to be maintained operational.

In a preferred embodiment, the mounting for electrical contact pins is mounted detachably on the distal end of the elongated pivotal arm.

By virtue of its detachability in this embodiment, the mounting for electrical contact pins can be easily removed and replaced to extend the life of the electroanalytical instrument.

In a preferred embodiment, the mounting for electrical contact pins comprises a flexible polymer body which sealingly encapsulates the electrical contact pins such that the electrical contact pins are protuberant from a front face of the body. The flexibility of the polymer body advantageously allows movement of the electrical contact pins so as to provide sufficient contact force between the electrical contact pins and the electrical contacts on the superior part of the electrochemical sensor.

The electrochemical sensor may be mounted in a slot in the anterior wall of the pivotal forearm. The inferior part of the electrochemical sensor may be outside the slot and the superior part of the electrochemical sensor may be inside the slot exposed through a window in the anterior wall.

Preferably in use, a slanted part of the front face of the flexible polymer body biasingly abuts the electrochemical sensor (e.g. through the window in the anterior wall).

In a preferred embodiment when the elongated pivotal arm is in the fully flexed position, the receptacle prevents the pivotal forearm from pivoting to the fully open position. Particularly preferably when the elongated pivotal arm is in the fully flexed position, the receptacle constrains the pivotal forearm to a partially open position sufficient to permit the electrochemical sensor to dismount from the anterior wall of the pivotal forearm. For this purpose, a part of the anterior wall may extend below the rim of and into the receptacle.

This embodiment allows partial opening to enable the electrochemical sensor to be safely released into the receptacle for disposal without exposing the operator to the electrochemical sensor or the electrical contact pins.

In a preferred embodiment, the elongated pivotal arm pivots restrainedly between an extended position (e.g., the fully extended position) and a flexed position (e.g., the fully flexed position).

By virtue of the elongated pivot arm pivoting restrainedly, the descent of the electrochemical sensor into the receptacle is retarded and the immersion of the electrochemical sensor in the aqueous sample is therefore controlled. This has demonstrable benefits for the dissolution of the reagent formulation from the electrochemical sensor and the resultant measurements. It also minimizes the risk of splash contamination.

Preferably the proximal end of the elongated pivotal arm is equipped with (e.g., configured into or attached to) a rotary sleeve which is mounted on an elongated shaft extending from the sealed housing, wherein the rotary sleeve and elongated shaft are sealingly spaced apart by a seal (e.g., a seal ring).

The frictional effect of the seal may be sufficient to ensure that the elongated pivotal arm pivots restrainedly with the advantages referred to hereinbefore.

In a preferred embodiment, the elongated pivotal arm pivots about a first axis between a fully extended position and a fully flexed position and the pivotal forearm pivots about a second axis between a fully open position and a fully closed position, wherein the first axis and second axis are substantially perpendicular.

The perpendicular axes of this embodiment serve to ensure advantageously that the pivotal forearm is unlikely to open during pivoting of the elongated pivotal arm.

Typically the pivotal forearm pivots medially between the fully open position and the fully closed position.

An interior compartment of the sealed housing may house a computer which interfaces with the potentiostat and provides a display.

The pivotal forearm may be retained in the fully closed position by a retaining catch. The retaining catch may be magnetic. The retaining catch may comprise a first part mounted on the anterior wall of the pivotal forearm cooperates with a second part mounted on the distal end of the elongated pivotal arm. The first part and second part may constitute a male and female part.

The electroanalytical instrument may further comprise a temperature probe extending inferiorly from an inferior face of the elongated pivotal arm whereby when the elongated pivotal arm is in the fully flexed position the temperature probe is immersed in the aqueous sample in the receptacle.

Preferably the electroanalytical instrument further comprises a switch which in response to an operating position of the elongated pivotal arm switches on the potentiostat, wherein the operating position is at or near to the fully flexed position. The switch may be a magnetically-operated switch (e.g., a reed switch) or an optically-operated switch.

In this embodiment, the switch ensures advantageously that potential is only applied to the electrical contact pins by the potentiostat when the electrochemical sensor is immersed in the aqueous sample and not (for example) when the elongated pivotal arm is an extended position for the pivotal forearm to be opened to clean the electrical contact pins.

The electroanalytical instrument may further comprise a removable lid on the receptacle. This may be useful to contain the aqueous sample and electrochemical sensor for disposal.

The receptacle may be configured to prevent overfill of an aqueous sample. For example, the receptacle may be configured to facilitate overflow to an overflow compartment when a threshold volume of aqueous sample is breached. This ensures a consistent volume of aqueous sample in the receptacle for electroanalysis.

For this purpose, the receptacle may be equipped with a notched wall which divides the internal chamber into a sample compartment and an overflow compartment. When a threshold volume of aqueous sample is breached in the sample compartment, there is an overflow of the aqueous sample to the overflow compartment.

The reagent formulation may include chemical components essential for specific ion electroanalysis such as a chemical reagent and a buffer. The chemical reagent may be a reductant essential for electroanalysis of a specific oxidant of interest. The reagent formulation is typically dried on the electrode surface. Once the electrochemical sensor is immersed in the aqueous sample, dissolution takes place to give rise to natural convection of the reagent formulation from the surface into the bulk sample.

Typically the reference electrode, counter electrode and at least one working electrode are microelectrodes.

n a preferred embodiment, the electrochemical sensor comprises:
an elongated substrate layer having a first end opposite to a second end;
first, second and third conductive tracks deposited axially onto the substrate layer in a parallel mutually spaced apart relationship, wherein the first conductive track constitutes a reference electrode, wherein on the second conductive track near to the second end of the substrate layer is a carbon deposit whereby to constitute a counter electrode and on the third conductive track near to the second end of the substrate layer is a carbon deposit whereby to constitute a working electrode, wherein each of the first, second and third conductive tracks terminates near to the first end of the substrate layer in an electrical contact; and a non-conductive layer deposited on the first, second and third conductive tracks, wherein the non-conductive layer is fabricated to fully expose each electrical contact near to the first end of the substrate layer, to fully expose the carbon deposit on the second conductive track near to the second end of the substrate layer, to fully expose the first conductive track near to the second end of the substrate layer and to partially expose discrete working regions of the carbon deposit of the third conductive track through an array of apertures, wherein the reagent formulation is deposited on or near to the surface of the working electrode.

The first conductive track may be between the second conductive track and the third conductive track.

The array of apertures may be fabricated in the non-conductive layer by a mechanical, chemical or physical removal technique such as ablation (e.g., photoablation) or etching. The array of apertures may be fabricated in the non-conductive layer by screen printing.

Each aperture may have a substantially regular shape. Typically, the apertures are uniformly shaped. Each aperture may be substantially circular or non-circular (e.g., rectangular or square). Preferably each aperture is substantially circular.

The array may adopt any suitable pattern (e.g., cubic or rectangular). The array may comprise 10 to 500 apertures, preferably 50 to 200 apertures, more preferably 80 to 120, most preferably about 95 apertures.

Preferably each aperture has a dimension (e.g., diameter) in the range 50 to 400 μm (e.g., about 350 μm).

Each aperture may be elongated (e.g., linear). Each elongated aperture may be substantially parallel to the first, second and third conductive track (e.g., vertical).

Preferably each elongated aperture is substantially perpendicular to the first, second and third conductive track (e.g., horizontal).

In a preferred embodiment, each aperture of the array of apertures is substantially rectangular (e.g., a microband). For example, each aperture may be microscopic in width (e.g., about 50 microns) and macroscopic in length.

In a preferred embodiment, the array of apertures is a substantially rectangular array In a preferred embodiment, the electrochemical sensor further comprises:

a fourth conductive track deposited axially onto the substrate layer, wherein the first, second, third and fourth conductive track are in a parallel mutually spaced apart relationship, wherein on the fourth conductive track near to the second end of the substrate layer is a carbon deposit whereby the third and fourth conductive tracks constitute a pair of working electrodes, wherein the first and second conductive tracks are flanked by the third and fourth conductive tracks, wherein each of the first, second, third and fourth conductive tracks terminates near to the first end of the substrate layer in an electrical contact, wherein the non-conductive layer is deposited on the first, second, third and fourth conductive tracks and is fabricated to fully expose each electrical contact near to the first end of the substrate layer, to fully expose the carbon deposit on the second conductive track near to the second end of the substrate layer, to fully expose the first conductive track near to the second end of the substrate layer and to partially expose discrete working regions of the carbon deposits of the third and fourth conductive tracks through an array of apertures, wherein the reagent formulation is deposited on or near to the surface of either or both of the pair of working electrodes.

Each aperture may be elongated (e.g., linear). Each elongated aperture may be substantially parallel to the first, second, third and fourth conductive track (e.g., vertical).

Preferably each elongated aperture is substantially perpendicular to the first, second, third and fourth conductive track (e.g., horizontal).

The non-conductive layer may be fabricated by a known deposition or growth technique such as printing (e.g., screen printing, silk screen printing, ink-jet printing or thick film printing), casting, spinning, sputtering, lithography, vapor deposition, spray coating or vacuum deposition. Preferably the non-conductive layer is fabricated by screen printing. The non-conductive layer may be composed of a non-conductive ink.

Each conductive track may be fabricated by a known deposition or growth technique such as printing (e.g., screen printing, silk screen printing or thick film printing), casting, spinning, sputtering, lithography, vapor deposition, spray coating or vacuum deposition. Each conductive track may be composed of an inert metal such as gold, silver or platinum. Each conductive track may be composed of a conductive ink such as silver or silver/silver chloride ink. The conductive ink may be printable.

The substrate layer may be a sheet or strip. The substrate layer is typically composed of an insulating polymer. The substrate layer may be composed of polyester, polycarbonate or polyvinyl chloride.

The carbon deposit on each conductive track may be deposited by known techniques such as printing (e.g., screen printing, silk screen printing, ink-jet printing or thick film printing), sputtering, lithography, vapor deposition, spray coating or vacuum deposition. The carbon deposit may be composed of inert carbon such as graphite, glassy carbon or pyrolytic carbon.

The aqueous sample may be potable water, recreational water, process water or waste water (e.g., industrial waste water).

Typically, the analyte is an oxidant of interest and the quantity of the oxidant of interest is its concentration. For this purpose, the reagent formulation includes a reductant.

Preferably the oxidant of interest is one or more of the group consisting of chlorine dioxide, chlorine, chlorite, hypochlorite, free chlorine, total chlorine, ozone, peracetic acid, hydrogen peroxide and monochloramine. Particularly preferably the oxidant of interest is free chlorine (and optionally total chlorine).

The reductant may be an iodide such as an alkali metal iodide (e.g., potassium iodide), N, N-diethyl-p-phenyldiamine (DPD) or tetramethylbenzidine (TMB).

The reagent formulation may further comprise one or more additives such as a buffer, gelling agent, thickening agent, wetting agent or stabilizer. Typical additives are one or more of the group consisting of sodium phosphate, potassium phthalate, sodium carbonate, disodium EDTA, hydroxylethylcellulose and polyvinylpyrrolidone. The reagent formulation may incorporate an acidic salt (eg sodium hydrogen sulphate) which in use reduces the pH to about 2.

The reagent formulation may take the form of a reagent layer. A reagent layer advantageously permits the redox reaction between the oxidant of interest and the reductant to occur intimately in situ.

The reagent formulation may be deposited and dried onto or near to the surface of either or both of the pair of working electrodes to form the reagent layer.

The reagent layer may include a porous matrix. The reagent layer may include a porous matrix impregnated with the reductant. The porous matrix may comprise polyvinylpyrrolidone and/or hydroxyethylcellulose. The reductant may be impregnated in the porous matrix by printing or micro-dosing.

In a preferred embodiment, the reagent formulation includes tetramethylbenzidine (TMB), a phosphate buffer and polyvinylpyrrolidone.

Viewed from a further aspect the present invention provides an electroanalytical instrument for determining by amperometry (e.g., chronoamperometry) the presence or quantity (e.g., concentration) of an analyte (e.g., an oxidant of interest) in an aqueous sample comprising:
 a sealed housing which is compartmentalized, wherein the sealed housing has an exterior compartment defining a receptacle for the aqueous sample and interior compartments;
 an elongated pivotal arm mounted pivotally at a proximal end on the sealed housing, wherein the elongated pivotal arm houses a potentiostat;
 a pivotal forearm joined pivotally to or near to a distal end of the elongated pivotal arm, wherein in use an electrochemical sensor is mounted in or on an anterior wall of the pivotal forearm and extends inferiorly to the elongated pivotal arm, wherein on an inferior part of the electrochemical sensor there are a reference electrode, a counter electrode and at least one working electrode which is dosed with a reagent formulation for electroanalysis and on a superior part of the electrochemical sensor each of the reference electrode, counter electrode and at least one working electrode terminates in an electrical contact; and
 electrical contact pins on the distal end of the elongated pivotal arm, wherein in use the electrical contact pins are electrically connected to the potentiostat and apply a potential to the electrochemical sensor,
 wherein the elongated pivotal arm pivots between a fully extended position and a fully flexed position whereat the inferior part of the electrochemical sensor is immersed in the aqueous sample in the receptacle thereby initiating dissolution of the reagent formulation into the aqueous sample and wherein the pivotal forearm pivots between a fully open position whereat the electrical contact pins are exposed and a fully closed position whereat the electrical contacts on the superior part of the electrochemical sensor are in operative contact with the electrical contact pins whereby when the elongated pivotal arm is in the fully flexed position and the pivotal forearm is in the fully closed position the electrochemical sensor interfaces the electrical contact pins and the aqueous sample,
 wherein when the elongated pivotal arm is in the fully flexed position, the receptacle constrains the pivotal forearm to a partially open position sufficient to permit the electrochemical sensor to dismount from the anterior wall of the pivotal forearm.

Viewed from a yet further aspect the present invention provides an electroanalytical instrument for determining by amperometry (e.g., chronoamperometry) the presence or quantity (e.g., concentration) of an analyte (e.g., an oxidant of interest) in an aqueous sample comprising:
 a sealed housing which is compartmentalized, wherein the sealed housing has an exterior compartment defining a receptacle for the aqueous sample and interior compartments;
 an elongated pivotal arm mounted pivotally at a proximal end on the sealed housing, wherein the elongated pivotal arm houses a potentiostat;
 a pivotal forearm joined pivotally to or near to a distal end of the elongated pivotal arm, wherein in use an electrochemical sensor is mounted in or on an anterior wall of the pivotal forearm and extends inferiorly to the elongated pivotal arm, wherein on an inferior part of the electrochemical sensor there are a reference electrode, a counter electrode and at least one working electrode which is dosed with a reagent formulation for electroanalysis and on a superior part of the electrochemical sensor each of the reference electrode, counter electrode and at least one working electrode terminates in an electrical contact; and
 electrical contact pins on the distal end of the elongated pivotal arm, wherein in use the electrical contact pins are electrically connected to the potentiostat and apply a potential to the electrochemical sensor,
 wherein the elongated pivotal arm pivots between a fully extended position and a fully flexed position whereat the inferior part of the electrochemical sensor is immersed in the aqueous sample in the receptacle thereby initiating dissolution of the reagent formulation into the aqueous sample and wherein the pivotal forearm pivots between a fully open position whereat the electrical contact pins are exposed and a fully closed position whereat the electrical contacts on the superior part of the electrochemical sensor are in operative contact with the electrical contact pins whereby when the elongated pivotal arm is in the fully flexed position and the pivotal forearm is in the fully closed position the electrochemical sensor interfaces the electrical contact pins and the aqueous sample,
 wherein the elongated pivotal arm pivots restrainedly between an extended position (e.g., the fully extended position) and a flexed position (e.g., the fully flexed position).

BRIEF DESCRIPTION OF THE DRAWINGS

The present invention will now be described in a non-limitative sense with reference to Examples and the accompanying Figures in which.

DETAILED DESCRIPTION

Figure 1:
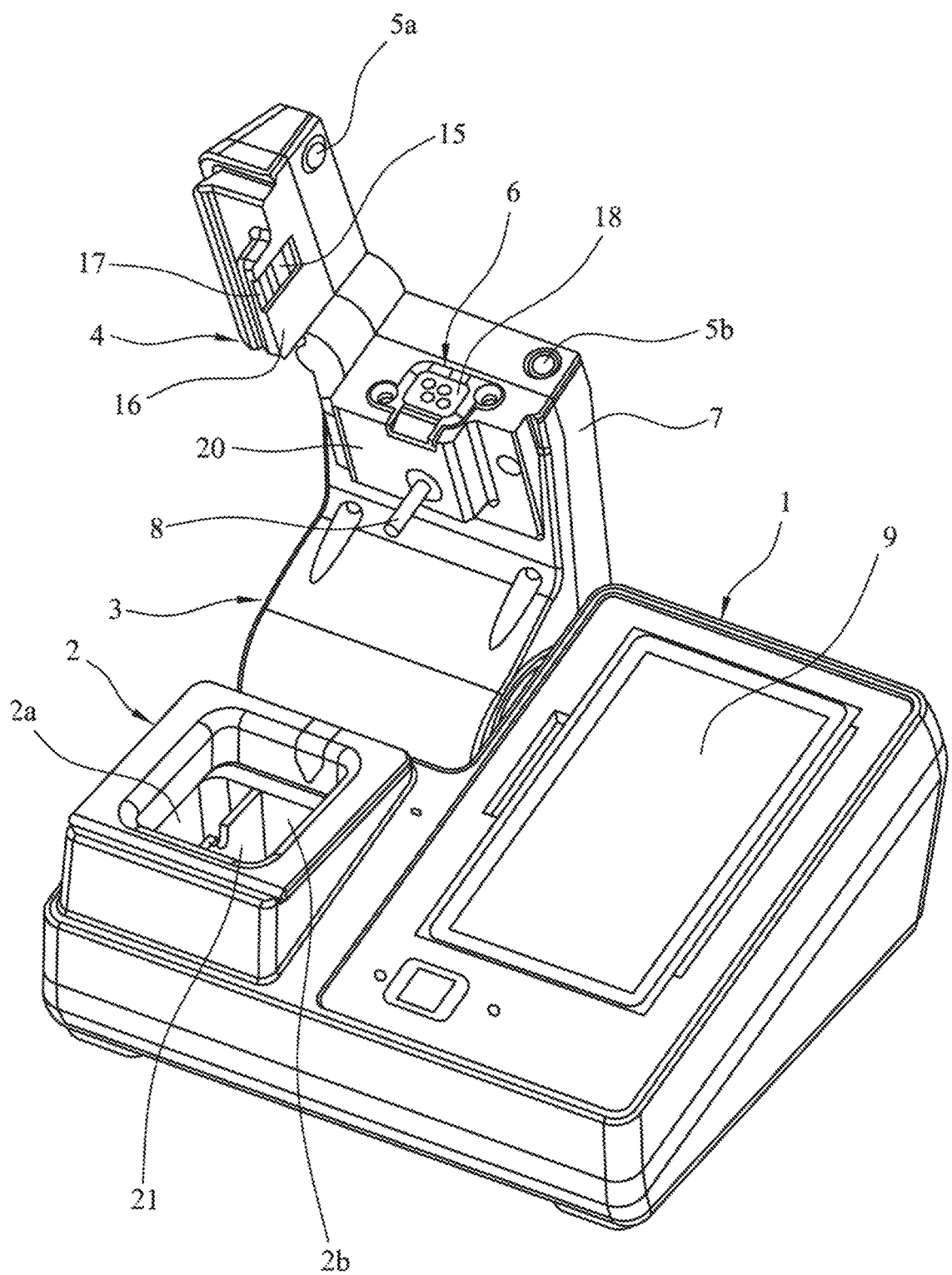
FIG. 1 is a front perspective view of an embodiment of the electroanalytical instrument of the invention.
Figure 2:
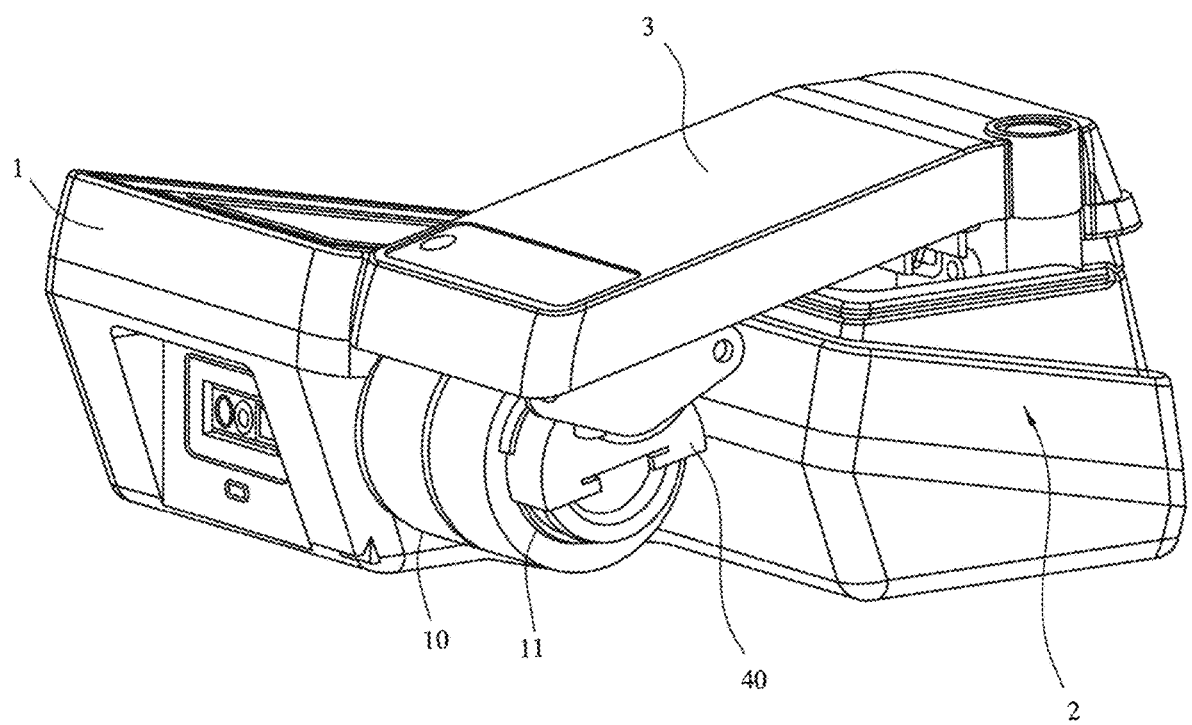
FIG. 2 is a rear perspective view of the embodiment of the electroanalytical instrument of the invention.

FIGS. 1 and 2 are front and rear perspective views respectively of an embodiment of the electroanalytical instrument of the invention. The electroanalytical instrument may be used to determine the concentration of an analyte of interest in an aqueous sample. Measurements are made by chronoamperometry and for this purpose, the instrument may be used in conjunction with an electrochemical sensor of the type disclosed in WO-A-2007/026152 which is commercially available. Such an electrochemical sensor is planar and consists of an inferior part where there is a reference electrode, a counter electrode and two working electrodes which are dosed with a reagent formulation for electroanalysis and a superior part where each of the reference electrode, counter electrode and working electrodes terminates in an electrical contact. For the sake of simplicity, an electrochemical sensor 100 is shown in the Figures without any detailed structure.

The electroanalytical instrument comprises a sealed housing 1 which is compartmentalised. An exterior compartment defines a receptacle 2 for the aqueous sample which contains the analyte of interest. An interior compartment of the sealed housing 1 houses a computer which provides a display 9. Other interior compartments of the sealed housing 1 house the electrical and electronic components necessary for electroanalytical measurements.

The receptacle 2 is equipped with a notched wall 21 which divides the internal chamber into a sample compartment 2b and an overflow compartment 2a. When a threshold volume of aqueous sample is breached in the sample compartment 2b, there is an overflow of the aqueous sample to the overflow compartment 2a.

An elongated pivotal arm 3 is mounted pivotally at a proximal end on the sealed housing 1. A distal part 7 of the elongated pivotal arm 3 houses a potentiostat. A mounting 6 for four electrical contact pins 18 is mounted sealingly on a distal end of the elongated pivotal arm 3.

A pivotal forearm 4 is joined pivotally to the distal end of the elongated pivotal arm 3. The electrochemical sensor 100 (not shown in FIGS. 1 and 2) is mounted in a slot 17 in an anterior wall 16 of the pivotal forearm 4 and extends inferiorly to the elongated pivotal arm 3. The inferior part of the electrochemical sensor 100 is outside the slot 17 and the superior part of the electrochemical sensor 100 is inside the slot 17 exposed through a window 15 in the anterior wall 16.

The elongated pivotal arm 3 pivots between a fully extended position (see FIG. 1) and a fully flexed position (see FIG. 2). In the fully flexed position, the inferior part of the electrochemical sensor 100 is immersed in the aqueous sample in the receptacle 2. The pivotal forearm 4 pivots medially between a fully open position (see FIG. 1) at which the electrical contact pins 18 are exposed and a fully closed position (see FIG. 2) at which the superior part of the electrochemical sensor 100 is in operative contact with the electrical contact pins 18. The axes about which the elongated pivotal arm 3 and pivotal forearm 4 pivot are perpendicular. When the elongated pivotal arm 3 is in the fully flexed position and the pivotal forearm 4 is in the fully closed position as shown in FIG. 2, the electrochemical sensor 100 interfaces the electrical contact pins 18 and the aqueous sample.

Figure 4:
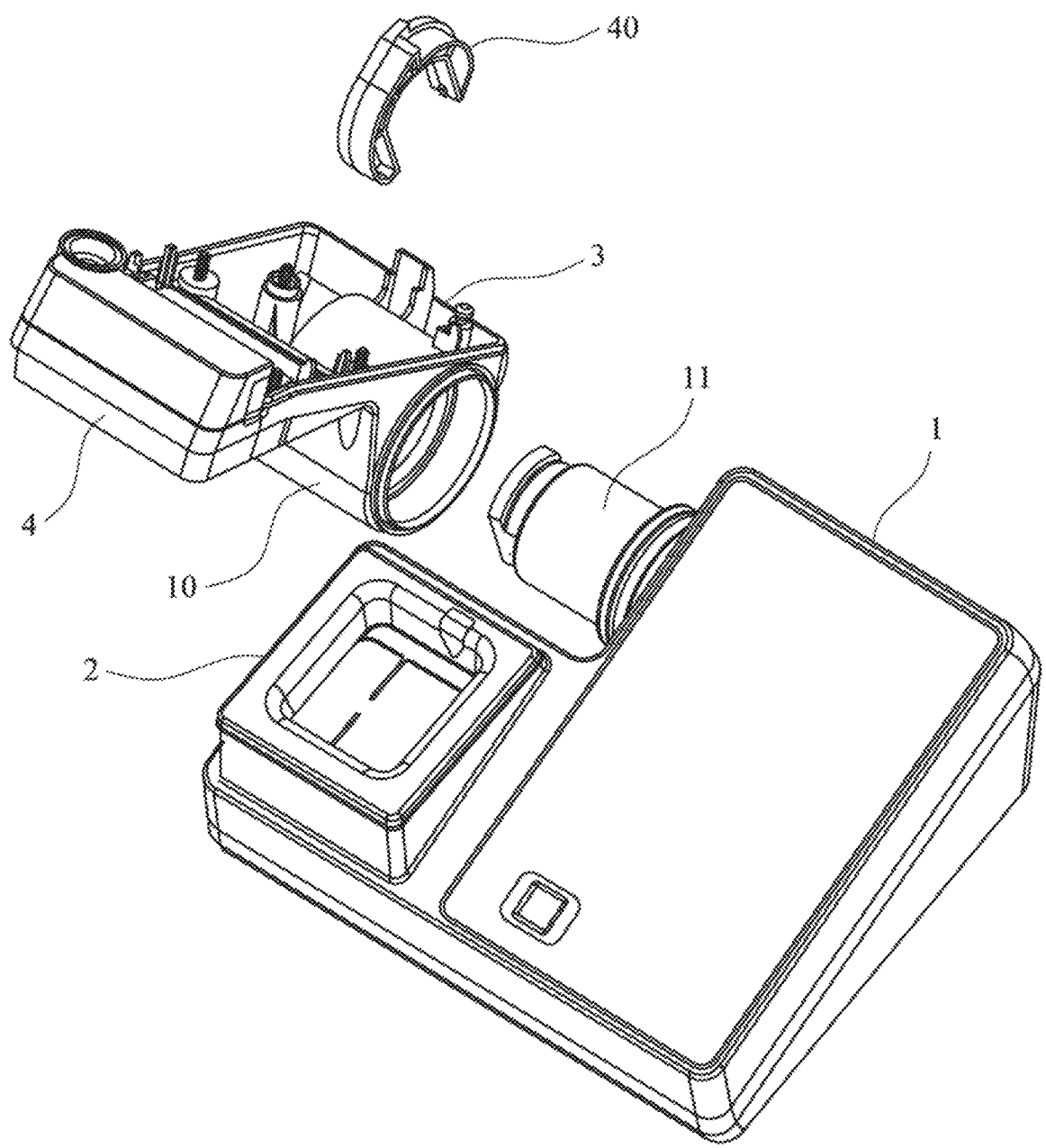
FIG. 4 is an exploded partial view of the embodiment of the electroanalytical instrument of the invention showing the pivotal mounting of the elongated pivotal arm and the housing.

As shown in FIG. 4, the proximal end of the elongated pivotal arm 3 is configured into a rotary sleeve 10 which is mounted on an elongated shaft 11 extending from the sealed housing 1. The rotary sleeve 10 is retained on the elongated shaft 11 by a retaining bracket 40. The rotary sleeve 10 and elongated shaft 11 are sealingly spaced apart by a seal ring. The frictional effect of the seal ring ensures that the elongated pivotal arm 3 pivots restrainedly between the fully extended position and the fully flexed position. This slows the descent of the electrochemical sensor 100 into the receptacle 2 and the immersion of the electrochemical sensor 100 in the aqueous sample is controlled. The benefits of this are demonstrated in the Example hereinafter.

Figure 5:
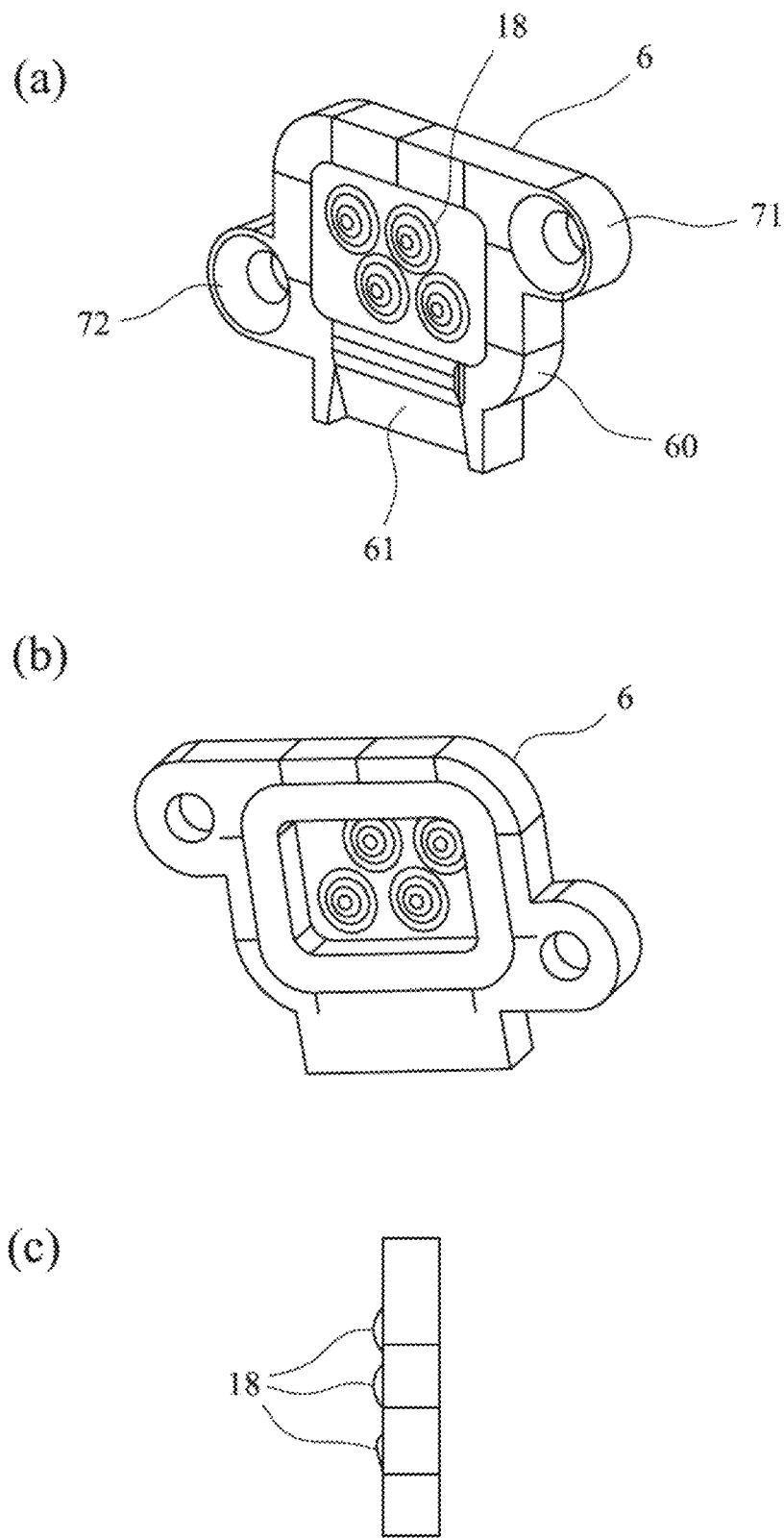
FIGS. 5(a) to (c) are views of a mounting for electrical contacts detached from the elongated pivotal arm.
FIGS. 5(d) and (e) are exploded partial views of the mounting and the pivotal forearm.
Figure 5:
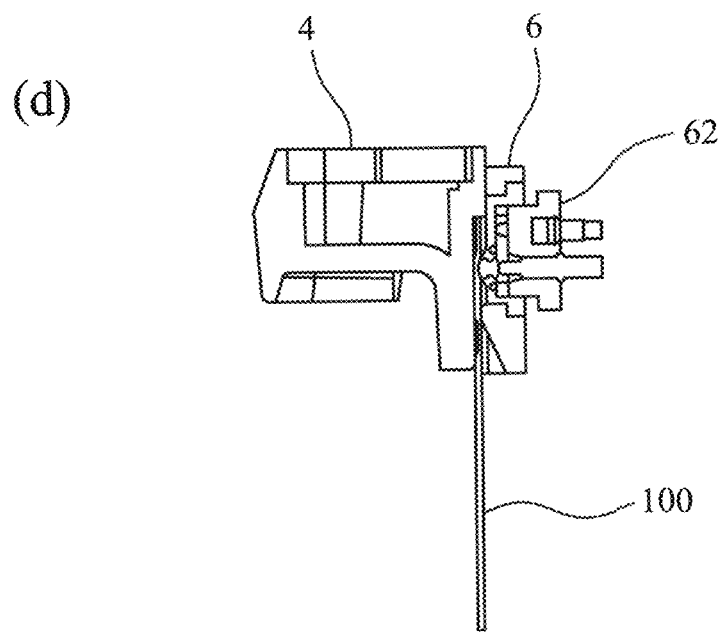
Figure 5:
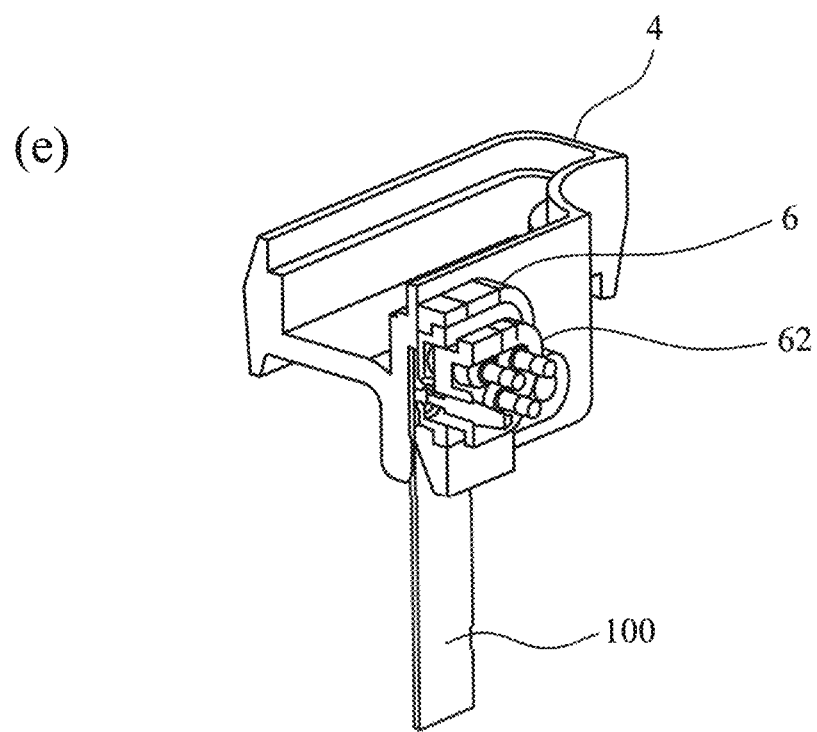

The mounting 6 for the electrical contact pins 18 is detachable from the elongated pivotal arm 3 and is shown detached in FIGS. 5a (front view), 5b (rear view) and 5c (side view). The mounting 6 comprises a flexible polymer body 60 which sealingly encapsulates the electrical contact pins 18 such that the electrical contact pins 18 are protuberant from a front face of the body 60 (see FIG. 5c). The electrical contact pins 18 are disposed in such a way as to be able to apply a potential to the electrical contacts of the reference electrode, counter electrode and working electrodes of the electrochemical sensor 100. The electrical contact pins 18 are electrically connected at the rear to the potentiostat by a connector 62 (see FIGS. 5(d) and (c). To enable the mounting 6 to be mounted flush with the distal end of the elongated pivotal arm 3, opposing corners of the flexible polymer body 60 are equipped with a socket 71, 72 to receive a threaded fastener.

Figure 6:
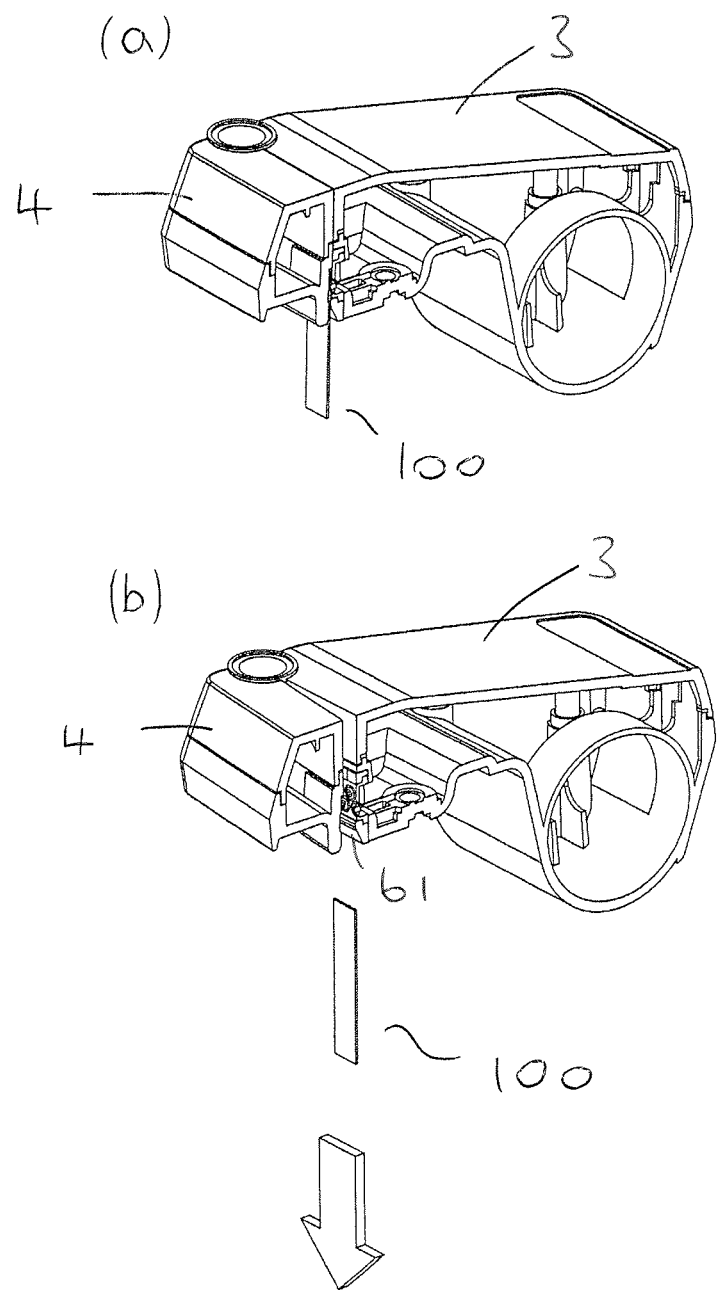
FIGS. 6(a) and (b) are exploded partial views of the pivotal forearm which shows the dismounting of an electrochemical sensor.

When the pivotal forearm 4 is fully dosed, the electrochemical sensor 100 can be forcibly inserted into slot 17 (see FIG. 6a). A slanted part 61 of the front face of the polymer body 60 abuts the electrochemical sensor 100 through the window 15 (see FIGS. 5c and 5d). By virtue of the flexibility of the polymer body 60, the abutment of the slanted part 61 and the electrochemical sensor 100 is biased so as to retain the electrochemical sensor in the slot 17.

The pivotal forearm 4 is retained in the fully closed position by a magnetic catch. A male part Sa of the magnetic catch is mounted on the anterior wall 16 of the pivotal forearm 4 and cooperates with a female part 5b of the magnetic catch mounted on the distal end of the elongated pivotal arm 3.

Figure 3:
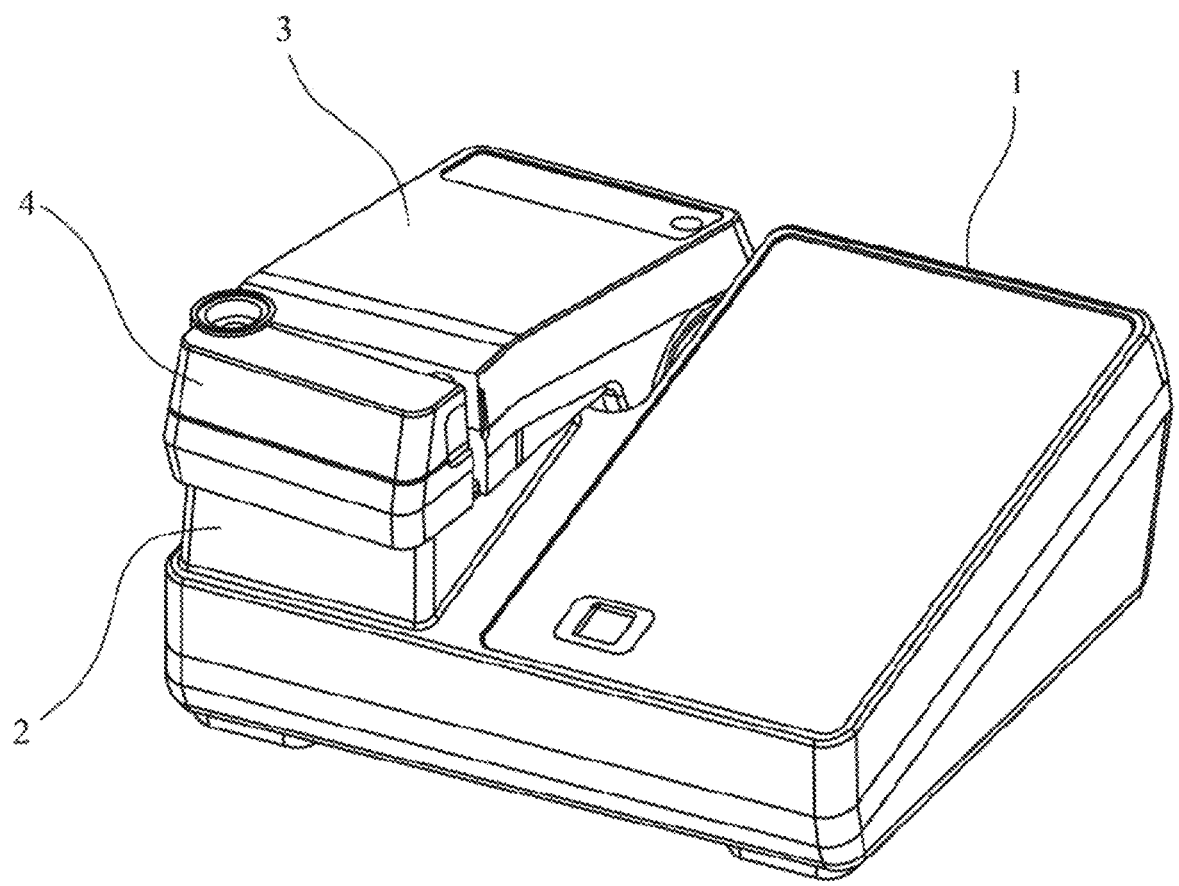
FIG. 3 is a front perspective view of the embodiment of the electroanalytical instrument of the invention with the pivotal forearm partially open.

When the elongated pivotal arm 3 is in the fully flexed position (see FIG. 3), the receptacle 2 constrains the pivotal forearm 4 to a partially open position. To achieve this, a part of the anterior wall 16 extends below the rim of and into the receptacle 2. In the partially open position, the slanted part 61 and the electrochemical sensor 100 are no longer in abutment and the electrochemical sensor 100 dismounts freely from slot 17 into the receptacle 2 without exposing the operator to the electrochemical sensor 100 or the electrical contact pins 18 (see FIG. 6b).

The electroanalytical instrument further comprises a reed switch or optical switch which in response to an operating position of the elongated pivotal arm 3 switches on the potentiostat. The operating position is at or near to the fully flexed position.

A temperature probe 8 extends inferiorly from an inferior face 20 of the elongated pivotal arm 3. When the elongated pivotal arm 3 is in the fully flexed position, the temperature probe 8 is immersed in the aqueous sample in the receptacle 2.

Example

An experiment was carried out to determine whether the manner in which electroanalysis was carried out could have an effect on the performance of an electrochemical sensor.

A 1.1 mg/L free chlorine solution was prepared and tested using a single batch of ChlorosenseR electrochemical sensors. Free chlorine readings were taken at immersion times* of 1 and 3 seconds.

(* immersion time is the time taken for the electrochemical sensor to fully immerse into the solution and the instrument to start the reading)

Results

Figure 7:
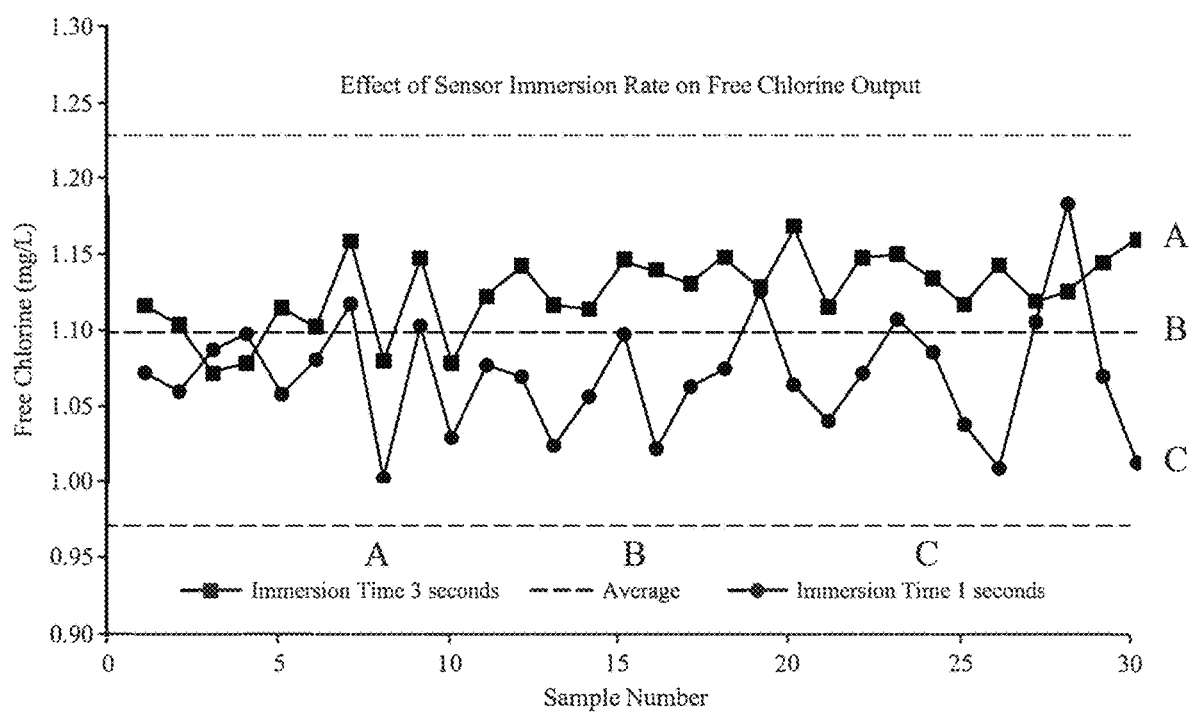
FIG. 7 shows the results of an experiment carried out to show the impact of immersion rate on the performance of an electrochemical sensor.

The results are presented in the Table below and in FIG. 7.

| Reading | Immersion Time 1 s | Immersion Time 3 s |
|---|---|---|
| 1 | 1.07 | 1.12 |
| 2 | 1.06 | 1.10 |
| 3 | 1.09 | 1.07 |
| 4 | 1.10 | 1.08 |
| 5 | 1.06 | 1.12 |
| 6 | 1.08 | 1.10 |
| 7 | 1.12 | 1.16 |
| 8 | 1.01 | 1.08 |
| 9 | 1.10 | 1.15 |
| 10 | 1.03 | 1.08 |
| 11 | 1.08 | 1.12 |
| 12 | 1.07 | 1.14 |
| 13 | 1.03 | 1.12 |
| 14 | 1.06 | 1.12 |
| 15 | 1.10 | 1.15 |
| 16 | 1.02 | 1.14 |
| 17 | 1.07 | 1.13 |
| 18 | 1.08 | 1.15 |
| 19 | 1.13 | 1.13 |
| 20 | 1.07 | 1.17 |
| 21 | 1.04 | 1.12 |
| 22 | 1.08 | 1.15 |
| 23 | 1.11 | 1.15 |
| 24 | 1.09 | 1.14 |
| 25 | 1.04 | 1.12 |
| 26 | 1.01 | 1.15 |
| 27 | 1.11 | 1.12 |
| 28 | 1.18 | 1.13 |
| 29 | 1.07 | 1.15 |
| 29 | 1.02 | 1.16 |

The results show that the performance of the electrochemical sensor is more consistent at an immersion rate of 3s than at an immersion rate of 1s. The electrochemical reagent begins to be released from the moment the electrochemical sensor contacts the free chlorine solution and disperses during the period of measurement. It is evident from this Example that the rate of immersion of the electrochemical sensor and the degree of agitation of the free chlorine solution during this period will affect the rate of dissolution and mixing of the reagent.

The invention claimed is:

1. An electroanalytical instrument for determining by amperometry the presence or quantity of an analyte in an aqueous sample comprising:
    a sealed housing which is compartmentalized, wherein the sealed housing has an exterior compartment defining a receptacle for the aqueous sample and interior compartments;
    an elongated pivotal arm mounted pivotally at a proximal end on the sealed housing, wherein the elongated pivotal arm houses a potentiostat;
    a pivotal forearm joined pivotally to or adjacent to a distal end of the elongated pivotal arm;
    an electrochemical sensor mounted in or on an anterior wall of the pivotal forearm extending inferiorly to the elongated pivotal arm, wherein on an inferior part of the electrochemical sensor there is a reference electrode, a counter electrode and at least one working electrode which is dosed with a reagent formulation for electroanalysis and on a superior part of the electrochemical sensor each of the reference electrode, each of the counter electrode and the at least one working electrode terminate in an electrical contact; and
    electrical contact pins provided on the distal end of the elongated pivotal arm, the electrical contact pins electrically connected to the potentiostat to apply a potential to the electrochemical sensor,
    the elongated pivotal arm configured to pivot between a fully extended position and a fully flexed position whereat the inferior part of the electrochemical sensor is immersed in the aqueous sample in the receptacle thereby initiating dissolution of the reagent formulation into the aqueous sample and wherein the pivotal forearm is pivotally joined to the distal end of the elongated pivotal arm such that the pivotal forearm is pivotable between a fully open position whereat the electrical contact pins are exposed and a fully closed position whereat the anterior wall of the pivotal forearm is positioned flush against the distal end of the elongated pivotal arm and the electrical contacts on the superior part of the electrochemical sensor are in operative contact with the electrical contact pins whereby when the elongated pivotal arm is in the fully flexed position and the pivotal forearm is in the fully closed position the electrochemical sensor is configured to interface with the electrical contact pins and the aqueous sample.

2. The electroanalytical instrument as claimed in claim 1 wherein a mounting for the electrical contact pins is mounted detachably on the distal end of the elongated pivotal arm.

3. The electroanalytical instrument as claimed in claim 1 wherein a mounting for the electrical contact pins comprises a flexible polymer body which sealingly encapsulates the electrical contact pins such that the electrical contact pins are protuberant from a front face of the flexible polymer body.

4. The electroanalytical instrument as claimed in claim 1 wherein in use, a slanted part of a front face of a flexible polymer body abuts and biases the electrochemical sensor.

5. The electroanalytical instrument as claimed in claim 1 wherein when the elongated pivotal arm is in the fully flexed position, the receptacle constrains the pivotal forearm to a partially open position sufficient to permit the electrochemical sensor to dismount from the anterior wall of the pivotal forearm.

6. The electroanalytical instrument as claimed in claim 1 wherein the elongated pivotal arm pivots restrainedly between the fully extended position and the fully flexed position.

7. The electroanalytical instrument as claimed in claim 1 wherein the proximal end of the elongated pivotal arm is equipped with a rotary sleeve which is mounted on an elongated shaft extending from the sealed housing, wherein the rotary sleeve and the elongated shaft are sealingly spaced apart by a seal.

8. The electroanalytical instrument as claimed in claim 1 wherein the elongated pivotal arm pivots about a first axis between the fully extended position and the fully flexed position and the pivotal forearm pivots about a second axis between the fully open position and the fully closed position, wherein the first axis and second axis are substantially perpendicular.

9. The electroanalytical instrument as claimed in claim 1 further comprising a switch which in response to an operating position of the elongated pivotal arm switches on the potentiostat, wherein the operating position is at or adjacent to the fully flexed position.

10. An electroanalytical instrument for determining by amperometry the presence or quantity of an analyte in an aqueous sample comprising:
a sealed housing which is compartmentalized, wherein the sealed housing has an exterior compartment defining a receptacle for the aqueous sample and interior compartments;
an elongated pivotal arm mounted pivotally at a proximal end on the sealed housing, wherein the elongated pivotal arm houses a potentiostat;
a pivotal forearm joined pivotally to or near to a distal end of the elongated pivotal arm, wherein in use an electrochemical sensor is mounted in or on an anterior wall of the pivotal forearm and extends inferiorly to the elongated pivotal arm, wherein on an inferior part of the electrochemical sensor there are a reference electrode, a counter electrode and at least one working electrode which is dosed with a reagent formulation for electroanalysis and on a superior part of the electrochemical sensor each of the reference electrode, counter electrode and at least one working electrode terminates in an electrical contact; and
electrical contact pins on the distal end of the elongated pivotal arm, wherein in use the electrical contact pins are electrically connected to the potentiostat and apply a potential to the electrochemical sensor,
wherein the elongated pivotal arm pivots between a fully extended position and a fully flexed position whereat the inferior part of the electrochemical sensor is immersed in the aqueous sample in the receptacle thereby initiating dissolution of the reagent formulation into the aqueous sample and wherein the pivotal forearm pivots between a fully open position whereat the electrical contact pins are exposed and a fully closed position whereat the electrical contacts on the superior part of the electrochemical sensor are in operative contact with the electrical contact pins whereby when the elongated pivotal arm is in the fully flexed position and the pivotal forearm is in the fully closed position the electrochemical sensor interfaces the electrical contact pins and the aqueous sample,
wherein when the elongated pivotal arm is in the fully flexed position, the receptacle constrains the pivotal forearm to a partially open position sufficient to permit the electrochemical sensor to dismount from the anterior wall of the pivotal forearm.

11. An electroanalytical instrument for determining by amperometry the presence or quantity of an analyte in an aqueous sample comprising:
a sealed housing which is compartmentalized, wherein the sealed housing has an exterior compartment defining a receptacle for the aqueous sample and interior compartments;
an elongated pivotal arm mounted pivotally at a proximal end on the sealed housing, wherein the elongated pivotal arm houses a potentiostat;
a pivotal forearm joined pivotally to or near to a distal end of the elongated pivotal arm, wherein in use an electrochemical sensor is mounted in or on an anterior wall of the pivotal forearm and extends inferiorly to the elongated pivotal arm, wherein on an inferior part of the electrochemical sensor there are a reference electrode, a counter electrode and at least one working electrode which is dosed with a reagent formulation for electroanalysis and on a superior part of the electrochemical sensor each of the reference electrode, counter electrode and at least one working electrode terminates in an electrical contact; and
electrical contact pins on the distal end of the elongated pivotal arm, wherein in use the electrical contact pins are electrically connected to the potentiostat and apply a potential to the electrochemical sensor,
wherein the elongated pivotal arm pivots between a fully extended position and a fully flexed position whereat the inferior part of the electrochemical sensor is immersed in the aqueous sample in the receptacle thereby initiating dissolution of the reagent formulation into the aqueous sample and wherein the pivotal forearm pivots between a fully open position whereat the electrical contact pins are exposed and a fully closed position whereat the electrical contacts on the superior part of the electrochemical sensor are in operative contact with the electrical contact pins whereby when the elongated pivotal arm is in the fully flexed position and the pivotal forearm is in the fully closed position the electrochemical sensor interfaces the electrical contact pins and the aqueous sample,
wherein the elongated pivotal arm pivots restrainedly between an extended position and a flexed position.

* * * * *